(12) United States Patent
Ostergard et al.

(10) Patent No.: US 8,287,478 B2
(45) Date of Patent: Oct. 16, 2012

(54) SHOULDER STABILIZING ORTHOTIC

(76) Inventors: Doak Ostergard, Lincoln, NE (US);
Bryan E. Kilbey, DeFuniak Sprs, FL (US)

( * ) Notice: Subject to any disclaimer, the term of this patent is extended or adjusted under 35 U.S.C. 154(b) by 325 days.

(21) Appl. No.: 12/854,368

(22) Filed: Aug. 11, 2010

(65) Prior Publication Data

US 2012/0041352 A1    Feb. 16, 2012

(51) Int. Cl.
*A61F 5/00* (2006.01)
*A61F 5/37* (2006.01)
*A61F 5/02* (2006.01)

(52) U.S. Cl. .................. 602/20; 2/45; 128/846

(58) Field of Classification Search ............ 602/20, 602/5, 1, 4; 128/846, 869, 870, 873, 874, 128/875; 2/459, 461, 44, 45, 268, 310
See application file for complete search history.

(56) References Cited

U.S. PATENT DOCUMENTS

| | | | | |
|---|---|---|---|---|
| 5,290,218 A * | 3/1994 | Kilbey | .............................. | 602/4 |
| 5,628,725 A * | 5/1997 | Ostergard | ........................ | 602/62 |
| 6,106,493 A * | 8/2000 | Rozell | ............................. | 602/20 |
| 6,440,094 B1 * | 8/2002 | Maas | .................................. | 602/5 |
| 7,081,101 B1 * | 7/2006 | Sawa | ............................... | 602/19 |
| 7,785,281 B2 * | 8/2010 | Scott | .................................. | 602/4 |

* cited by examiner

*Primary Examiner* — Loan Thanh
*Assistant Examiner* — Tarla Patel
(74) *Attorney, Agent, or Firm* — J. Wiley Horton

(57) ABSTRACT

A multi-layered orthosis designed to stabilize the human shoulder joint. A base harness includes a shoulder enclosure, an anterior panel, and a posterior panel. An adjustable break separates free ends of the anterior and posterior panels which are distal to the shoulder enclosure. The base harness is applied to a patient by slipping the shoulder enclosure around the affected shoulder. Anterior and posterior straps are passed over the deltoid region of the affected shoulder and secured to the base harness. An additional large strap is placed over the anterior and posterior straps.

27 Claims, 18 Drawing Sheets

SHOULDER STABILIZING ORTHOTIC

BACKGROUND OF THE INVENTION

1. Field of the Invention

This invention relates to the field of medical products. More specifically, the invention comprises 2. Description of the Related Art

BRIEF SUMMARY OF THE PRESENT INVENTION

The present invention comprises a multi-layered orthosis designed to stabilize the human shoulder joint. A base harness includes a shoulder enclosure, an anterior panel, and a posterior panel. An adjustable break separates free ends of the anterior and posterior panels which are distal to the shoulder enclosure. The base harness is applied to a patient by slipping the shoulder enclosure around the affected shoulder. The distal ends of the anterior and posterior panels are then passed around the axilla of the non-affected shoulder and the anterior and posterior panels are secured together. A bicep closure is preferably used to lock the shoulder enclosure in position.

Anterior and posterior straps are anchored to the lower portion of the shoulder enclosure. The posterior strap passes over the deltoid region of the affected shoulder, across the patient's back, and attaches to an anchor point which is near the axilla of the non-affected shoulder. The anterior strap passes over the deltoid region of the affected shoulder, across the patient's chest, and attaches near or on the same anchor point.

Once the anterior and posterior straps are applied, a separate A/P strap is attached to the lower portion of the shoulder enclosure. This A/P strap may then be applied in different ways, depending on the particular shoulder instability being treated. The components are preferably equipped with convenient fastening devices, such as hook and loop fasteners. The exterior of the base harness and various straps may be covered with loop material so that appropriately positioned hook material can be used to secure the straps in many different positions.

The invention allows the patient a nearly-full range of motion for the affected shoulder, while maintaining stability of the joint. It is particularly useful in stabilizing dislocations, and will allow an athlete such as a football player to continue playing after a dislocation injury. The athlete will generally need surgery to correct damage within the shoulder joint, but the orthosis will allow the player to safely continue playing until such time as surgery can be performed.

Figure 1:
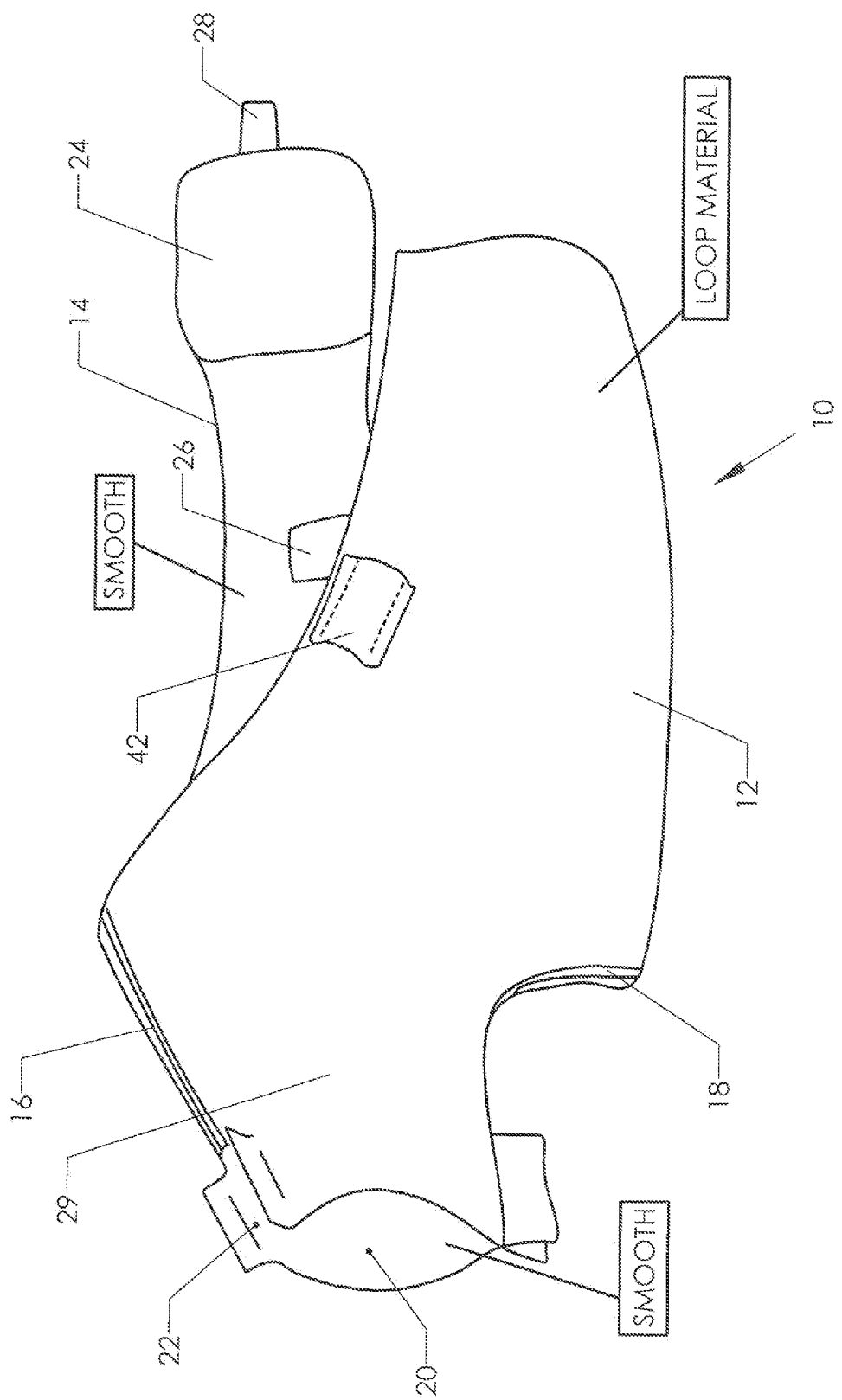
FIG. 1 is a perspective view, showing the first layer of the present invention from an anterior vantage point.

| REFERENCE NUMERALS IN THE DRAWINGS | | | |
|---|---|---|---|
| 10 | base harness | 12 | anterior panel |
| 14 | posterior panel | 16 | dorsal seam |
| 18 | ventral seam | 20 | bicep opening |
| 22 | bicep adjustment gap | 24 | hook panel |
| 26 | hook panel | 28 | pull tab |
| 29 | shoulder enclosure | 30 | anchor panel |
| 32 | pivoting buckle | 34 | pivoting buckle |
| 36 | pivot | 38 | pivot |
| 40 | posterior guide loop | 42 | anterior guide loop |
| 44 | interlock opening | 46 | hook panel |
| 50 | anterior strap | 52 | posterior strap |
| 53 | hook panel | 56 | axilla anchor region |
| 58 | hook panel | 60 | patient |
| 62 | shoulder stabilizing orthosis | 64 | axilla |
| 66 | arm | 68 | torso |
| 70 | A/P strap | 72 | butterfly hook panel |
| 74 | butterfly | 76 | hook panel |
| 78 | hook panel | 80 | ventral attachment |
| 82 | hook patch | 84 | cover |
| 86 | hook panel | | |

DETAILED DESCRIPTION OF THE INVENTION

Figure 2:
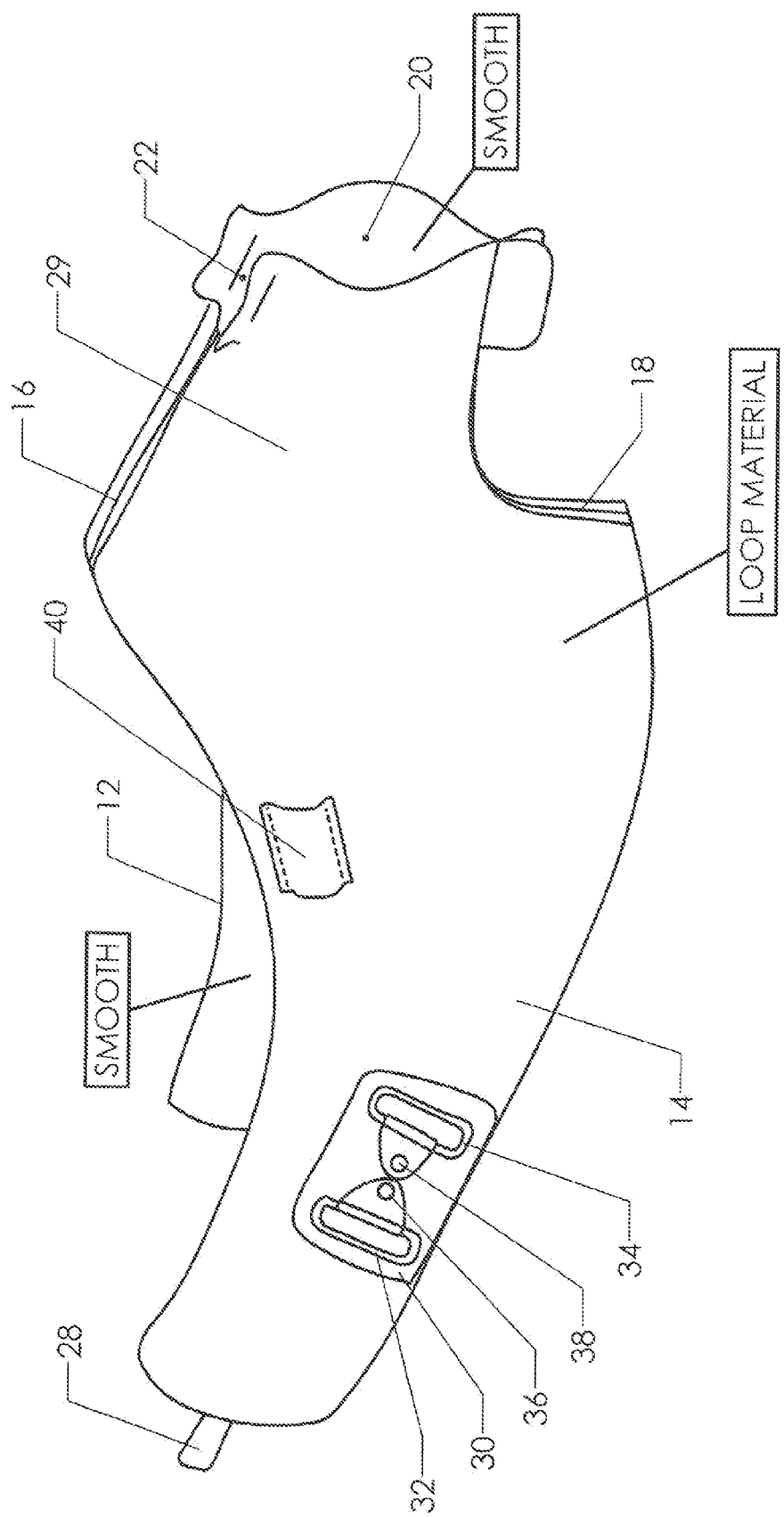
FIG. 2 is a perspective view, showing the first layer of the present invention from a posterior vantage point.

The Shoulder stabilizing Orthosis uses multiple layers of elastic material to secure an unstable or otherwise affected shoulder joint while simultaneously allowing the joint a significant range of motion. FIGS. 1 and 2 show the "base" layer. Base harness 10 is preferably made of at least two layers of fabric, both of which preferably stretch in all directions.

The base harness will often be applied directly to the user's skin, beneath the first layer of conventional clothing. Thus, the inward facing surface of the base harness is preferably smooth and comfortable against the skin. The harness will often be worn in athletic competition, so it should accommodate perspiration. The inward facing material ideally (1) allows perspiration to escape; (2) provides a reasonably high coefficient of friction so that the harness will not move excessively; and (3) is comfortable to the wearer.

The outer surface is used to secure various hook-and-loop type fastening patches—as will be described subsequently.

Thus, it is preferable to cover a large portion of the outward facing surface with loop material (and in fact the entire outward facing surface can be covered in loop material).

Those skilled in the art will know that many different patterns could be used to develop the geometry needed for the base harness. FIGS. 1 and 2 show one example, in which two separate fabric assemblies (anterior panel 12 and posterior panel 14) are joined along dorsal seam 16 and ventral seam 18 to form shoulder enclosure 29. The shoulder enclosure is configured to slide over the affected shoulder and encompass the associated bicep area of the upper arm. The anterior panel and the posterior panel have free ends distal to shoulder enclosure 29. The free ends' form a break in the encircling band of the base harness which allows the base harness to be applied to a user (as will be explained subsequently).

The geometry of the upper arm varies considerably from patient to patient. Thus, size adjusting features are preferably included. One way to accommodate the anticipated variation is to provide an open bicep adjusting gap 22 proximate bicep opening 26. Closure features can be provided to change the diameter of the bicep opening, as will be disclosed subsequently.

Posterior panel 14 includes an inward-facing hook panel 24, with associated pull tab 28. Hook panel 24 is designed to releasably engage the loop material on the outward-facing surface of anterior panel 12 when the base harness is placed on a patient. Anterior guide loop 42 is provided to locate additional features which will be described subsequently.

FIG. 2 shows the posterior side of base harness 10. The reader will observe how—in this embodiment—posterior panel 14 is joined to the anterior panel along dorsal seam 16 and ventral seam 18. Posterior guide loop 40 is provided to locate another strapping feature. Anchor panel 30 is attached to the anterior panel approximately in the position shown. The anchor panel includes pivoting buckle 32 and pivoting buckle 34. In this version, the two buckles are pivotally connected to the anchor panel by pivot 36 and pivot 38, respectively. The reader will note how the inward facing surface of the base harness is preferably smooth while the outward facing surface is preferably covered in loop material so that various hook patches may be easily attached in virtually any desired location. The simplest way to do this is to make the anterior panel and the posterior panel as assemblies of two pieces of fabric (one facing inward and one facing outward). However, it is also possible to provide a single piece of fabric having the desired characteristics on the inward facing and outward facing surfaces.

Figure 3:
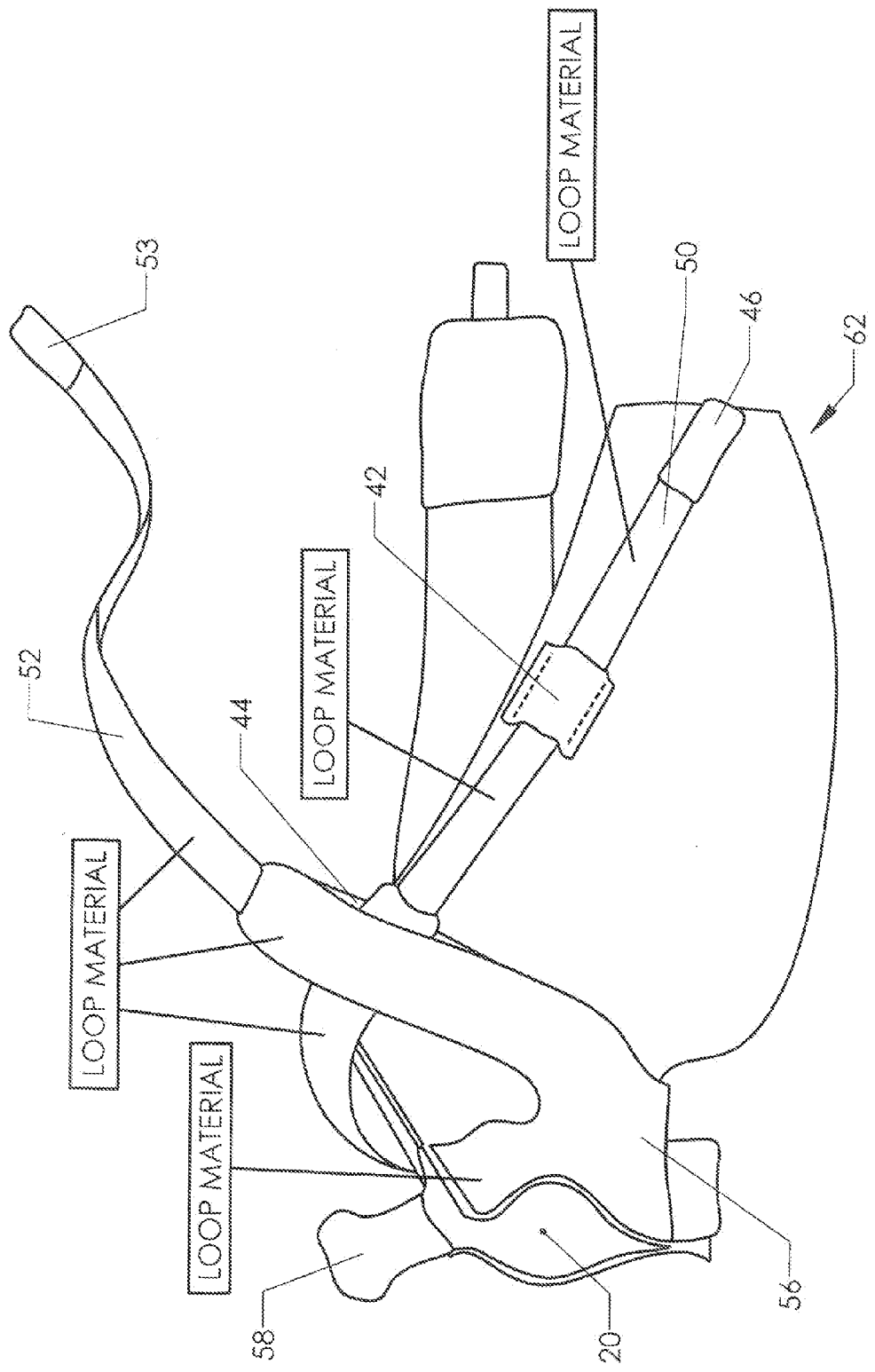
FIG. 3 is a perspective view, showing the addition of an intermediate layer to the present invention.

FIG. 3 shows the base harness with the addition of a second layer of securing devices. Posterior strap 52 is anchored to the lower part of the shoulder enclosure in axilla anchor region 56. It is configured to cross over the deltoid region of the affected shoulder and then over the patient's back. Anterior strap 50 is also anchored to the lower part of the shoulder enclosure (on the posterior side, which is hidden in the view). It wraps over the deltoid region of the affected shoulder and then passes over the patient's chest. The straps can be made of elastic or inelastic material, though in many instances a material having some elasticity is preferable.

The anterior and posterior straps can be attached to the base harness using any suitable means. One good method is to sew them together with the anterior and posterior panels in forming ventral seam 18, but many other methods can be used (including hook and loop type fasteners).

The invention allows the stabilization of the shoulder joint by initially providing a surrounding and reinforcing base harness that is then supplemented by the addition and adjustment of the anterior and posterior straps. The initial encapsulation by the base harness holds the shoulder in a stable position while the other straps are adjusted—which represents a significant advantage for the practitioner. The anterior and posterior straps are preferably affixed to the base harness so that the practitioner does not need to keep track of separate components.

It is preferable for the anterior and posterior straps to remain in a specified location on the patient. In most instances, it is desirable to have them cross in the deltoid region of the affected shoulder. However, as the patient moves the affected arm, there is a natural tendency for the straps to slip downward into the bicep region or upward into the neck region. To combat this tendency, the two straps are preferably linked together ("interlocked") where they cross. FIG. 3 shows one way to provide such a linkage. Posterior strap 52 includes interlock opening 44 passing completely therethrough. Anterior strap 50 passes through interlock opening 44, thereby linking the two straps together.

Guide loop 42 is provided to properly locate anterior strap 50 while posterior guide loop 40 (shown in FIG. 2) is used to properly locate posterior strap 52—as will be explained. FIG. 3 shows that anterior strap 50 includes hook panel 46 proximate its end, while posterior strap 52 includes hook panel 53 proximate its end. The assembly of the base harness and the two straps is then referred to as shoulder stabilizing orthosis 62.

Hook panel 58 is provided proximate the bicep adjustment gap. Once the orthosis is in place on the patient, hook panel 58 may be used to tighten the bicep opening to a desired degree. It can then be pressed onto the loop material on the exterior of posterior strap 52, thereby securing the bicep opening.

Figure 4:
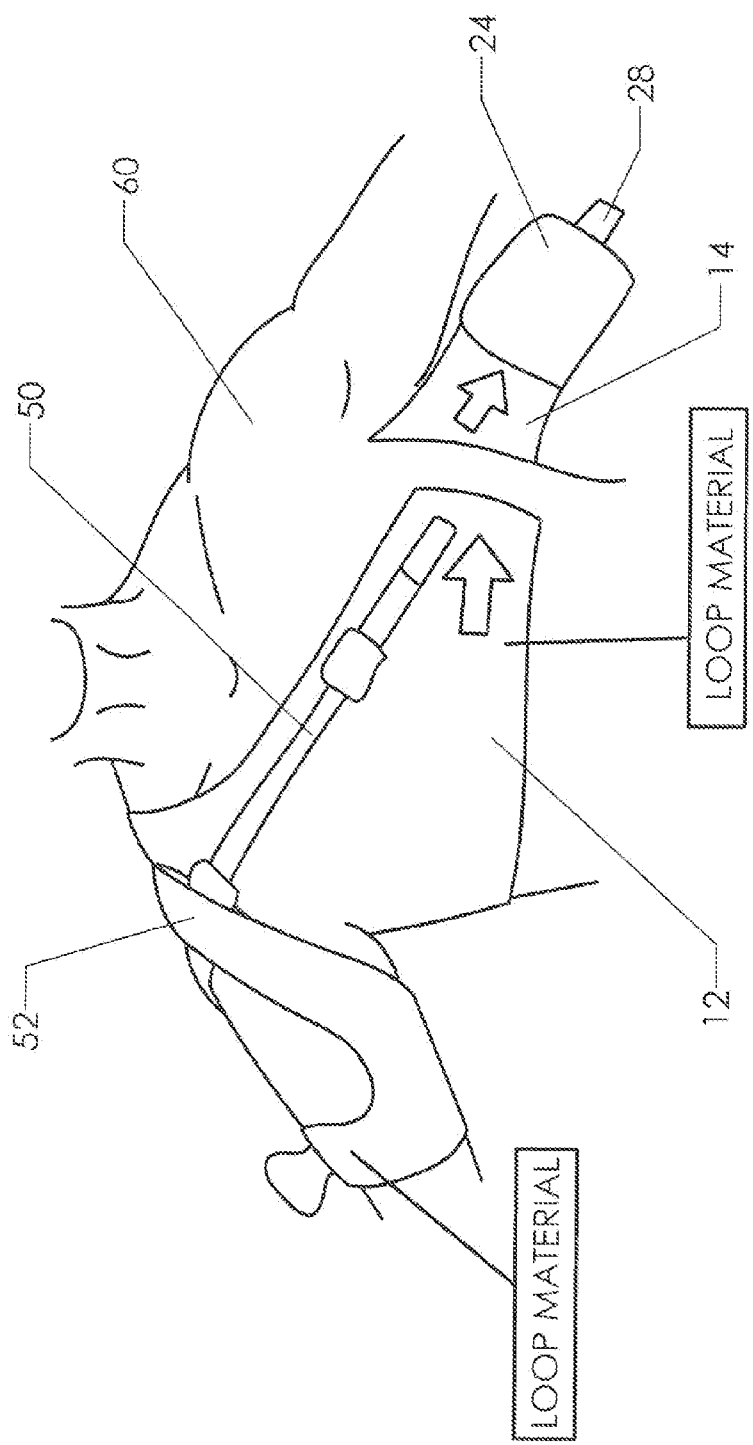
FIG. 4 is an anterior elevation view, showing the application of the invention to a patient.

FIGS. 4 through 9 explain how the orthosis is applied to a patient. The orthosis can be applied to either shoulder. Alternatively, mirrored versions of the orthosis can be supplied which are particularly configured to apply to the right shoulder or the left shoulder. In FIG. 4, the patient has an issue with his right shoulder, so the orthosis is applied to that side. The shoulder enclosure is pulled over the right shoulder and pulled up and over the deltoid region. The bicep adjustment is made and hook panel 58 is secured to secure the shoulder enclosure to the arm (Securing the bicep adjustment prevents the shoulder enclosure from sliding up the arm when the balance of the orthosis is secured). The free end of the posterior panel is then passed under the opposite arm and stretched toward the free end of anterior panel 12. The user may stretch the anterior panel by grasping and pulling pull tab 28.

Figure 5:
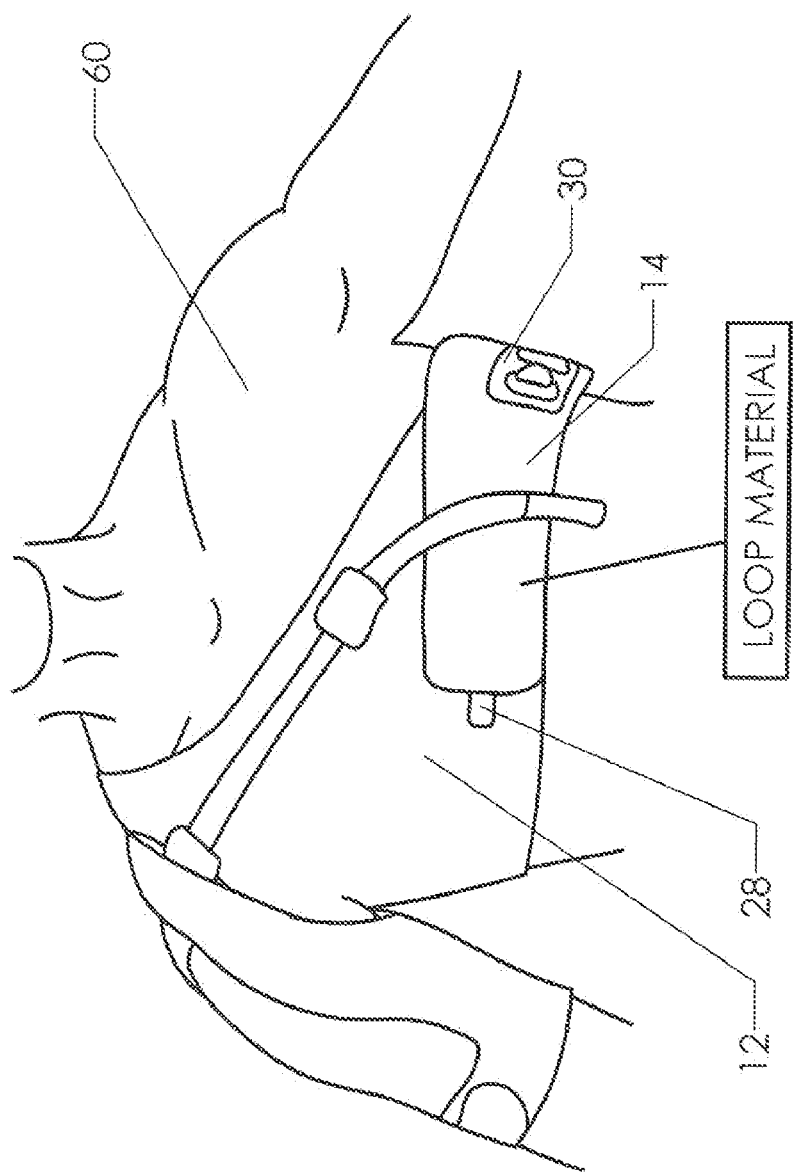
FIG. 5 is an anterior elevation view, showing the application of the invention to a patient.

Hook panel 24 is posited to wrap over and engage the loop material on the exterior of anterior panel 12. FIG. 5 shows the base harness in place, with the anterior and posterior panels linked together. The user applying the brace will preferably stretch the panels until anchor panel 30 lies roughly beneath the axilla ("armpit") of the unaffected shoulder of patient 60. The reader will note that anterior strap 50 is at this point dangling loose. The posterior strap is loose as well.

Figure 6:
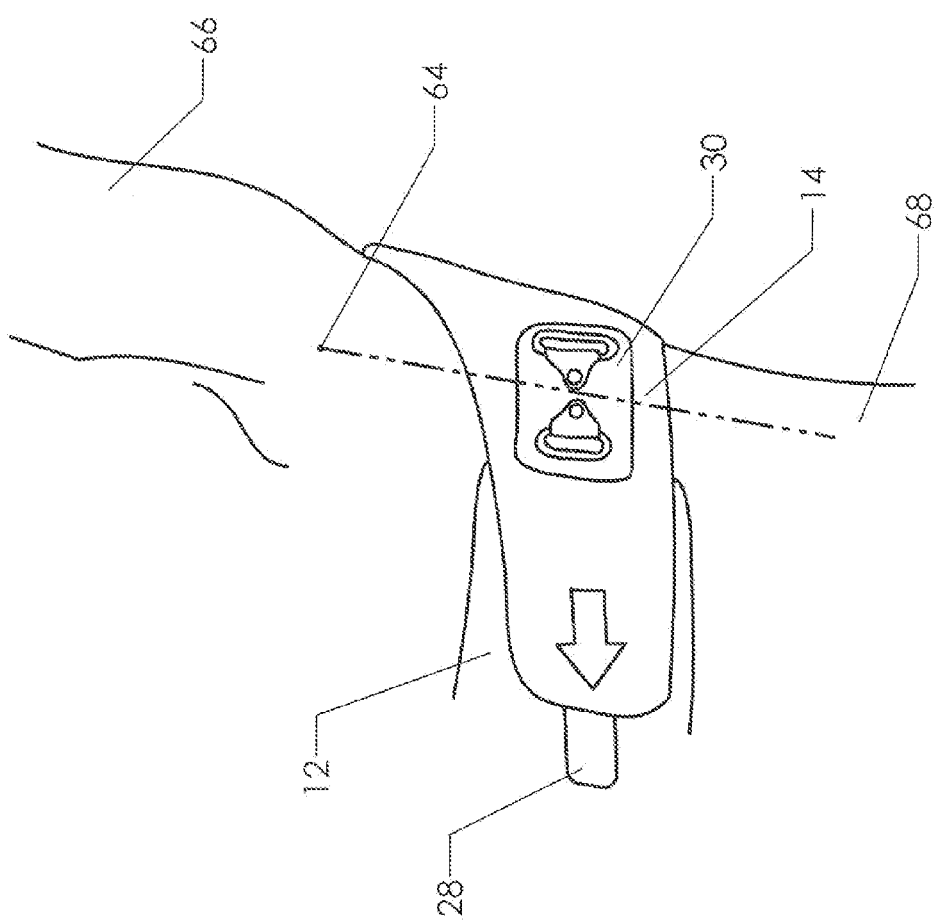
FIG. 6 is a perspective view of the patient's axilla region on the non-affected side, showing the application of the invention.

The next step is properly positioning and securing the anterior and posterior straps. Turning to FIG. 6, the user preferably makes fine adjustments to the securing of the posterior panel 14 to the anterior panel 12 such that the centerline of anchor panel 30 lies approximately beneath axilla 64 of the unaffected arm. FIG. 6 depicts this as an axis running down from axilla 64 through the midline of torso 68. The word "approximately" is used because the variability of human anatomy means that the medical practitioner must allow some accommodation for shoulder shape, chest shape, etc. The anchor panel 30 is preferably located so that this imaginary axis runs down the center of the panel. A single user may easily grab the free end of the posterior panel (using pull tab 28) and "fine tune" the position of the joint between the two panels so that the anchor panel lies in the preferred position. Once the anchor panel is properly located, the anterior and posterior straps may be adjusted and secured.

Returning briefly to FIG. 1, the reader will observe hook panel 26 located on the inward facing surface of posterior panel 14. This feature can be used to temporarily secure base harness 10 around the patient's chest while the position of the harness is adjusted. Once the adjustment is made satisfactorily hook panel 24 can be pressed into the loop material on anterior panel 12 to complete the process.

Figure 7:
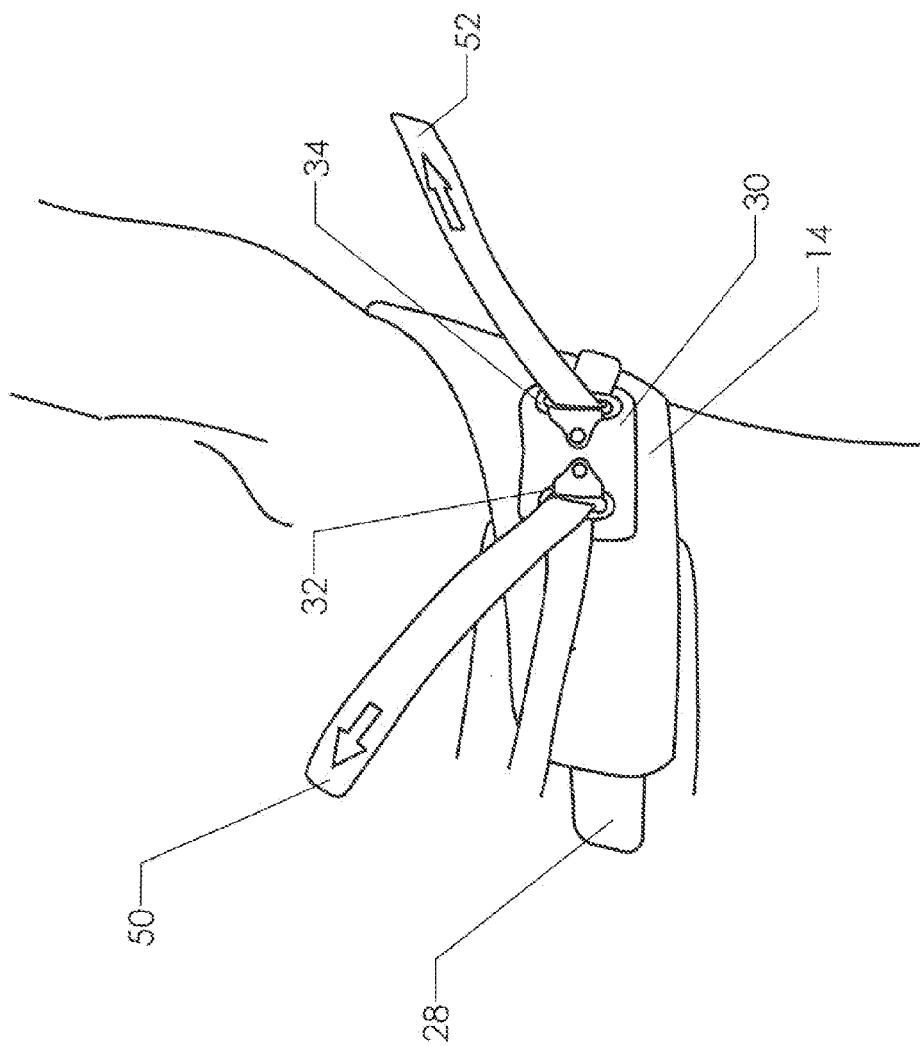
FIG. 7 is a perspective view showing the same area as FIG. 6, with the addition of the anterior and posterior straps.

FIG. 7 shows how anterior strap 50 is looped through pivoting buckle 32, while posterior strap 52 is looped through pivoting buckle 34. Hook panel 46 on the anterior strap is now facing toward the loop material on the strap (The hook panel is facing away from the viewer and is not visible in FIG. 7). Likewise, hook panel 53 on the posterior strap is now facing toward the loop material on the strap. The two straps are advanced through the two pivoting buckles as indicated by the arrows in FIG. 7.

Figure 8:
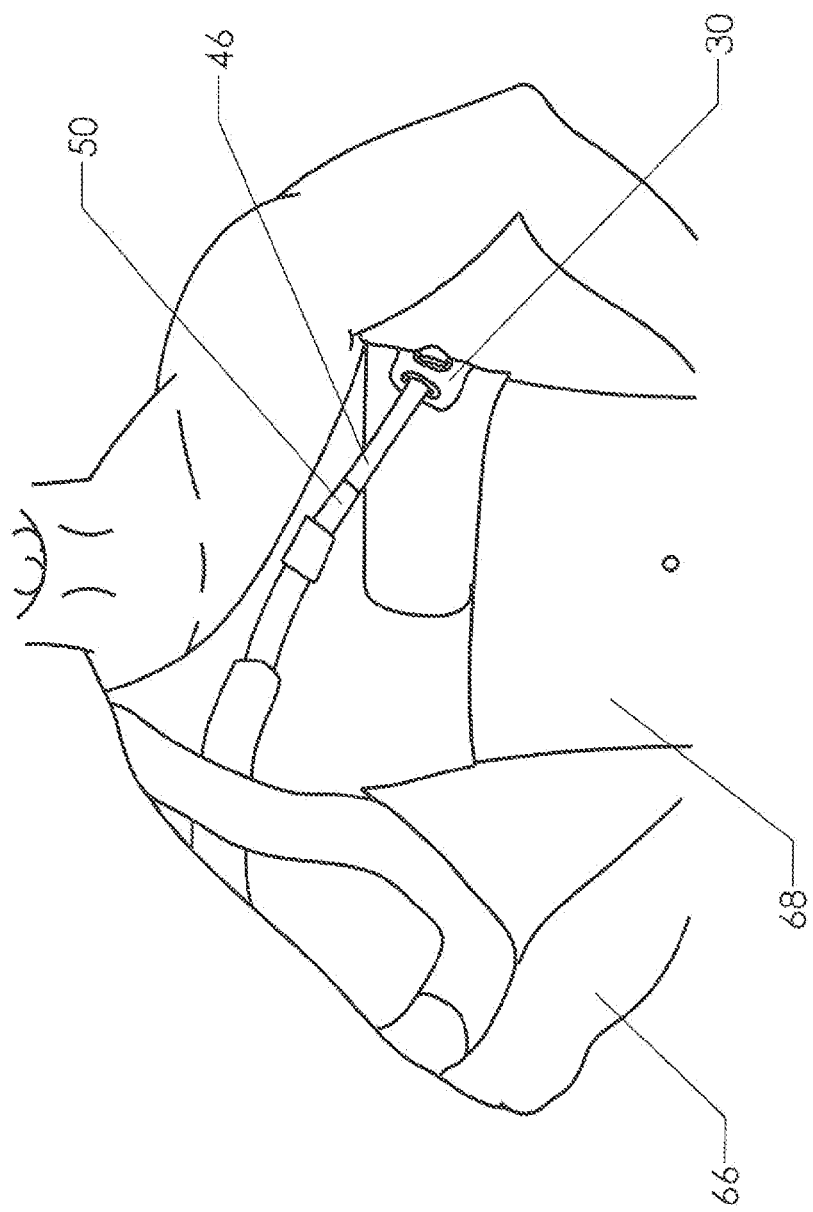
FIG. 8 is an anterior elevation view, after the anterior and posterior straps have been secured.

FIG. 8 shows an anterior view of the patient. Arm 66 is preferably positioned as shown with respect to torso 68 (though the actual positioning will be done at the discretion of the user dependent upon the shoulder condition being stabilized). Anterior strap 50 is tightened by pulling it through the pivoting buckle. When the desired tightness is achieved, hook panel 46 (which is facing away from the viewer in FIG. 8) on the end of the anterior strap is pressed into the loop material on the side of the strap facing the viewer and thereby secured. Alternatively, hook panel 46 may be pressed against the loop material on any other convenient outward-facing surface of the orthosis (since it is preferably covered in loop material).

Figure 9:
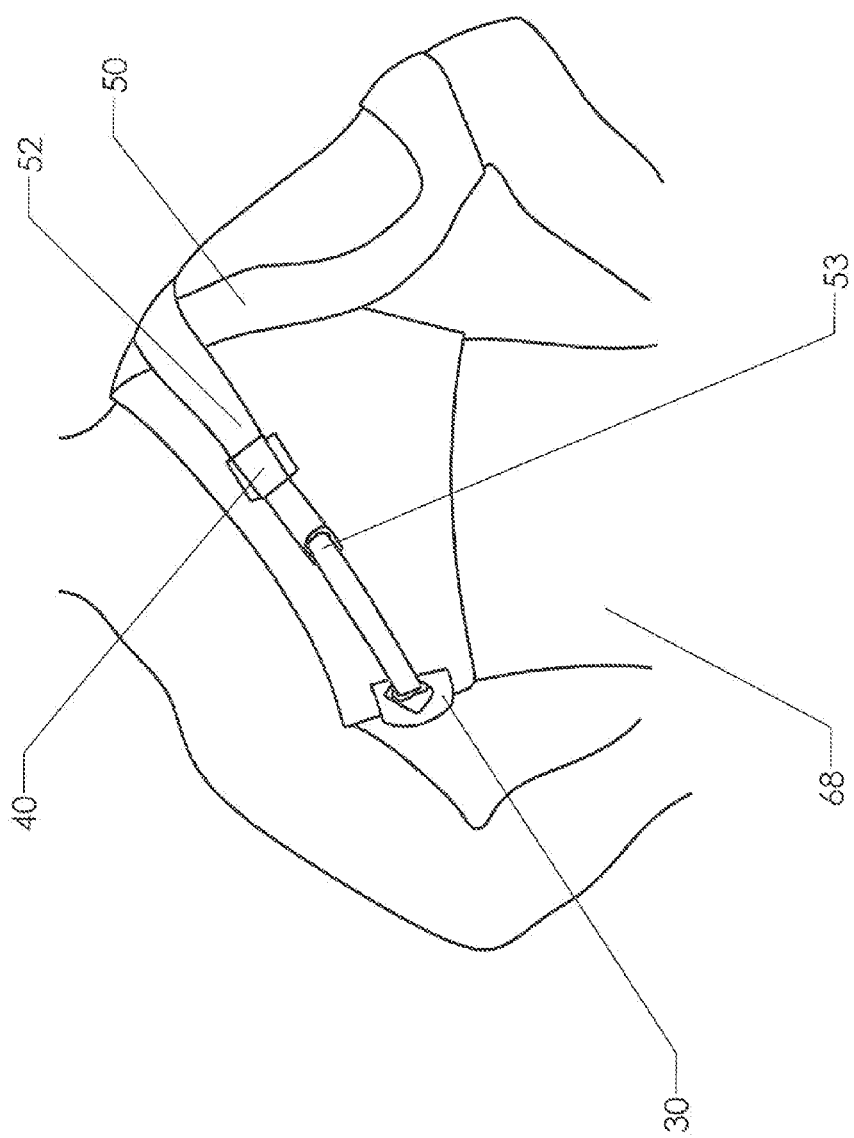
FIG. 9 is a posterior elevation view, after the anterior and posterior straps have been secured.

Those skilled in the art will realize that the use of the buckle gives the user a 2 to 1 mechanical advantage in tightening anterior strap 50. FIG. 9—a posterior view of the patient—shows a similar operation being performed for posterior strap 52. It is positioned and hook panel 53 (facing away from the viewer) is pressed into position against the corresponding loop material on the outward facing surface of the posterior strap or at some other convenient location on the orthotic. Posterior guide loop 40 helps to maintain the proper position for the posterior strap (as the anterior guide loop 42 does for the anterior strap).

Looking at FIGS. 8 and 9, those skilled in the art will realize that the tightening of the anterior and posterior straps may become an iterative process. If one is fully tightened while the other remains slack, then anchor panel 30 will be pulled out of its preferred position beneath the axilla of the unaffected shoulder. Thus, it is desirable to iteratively tighten the anterior and posterior straps while maintaining the correct position of the anchor panel. Once they are fully tightened, the user proceeds to the next step.

It is preferable for each strap to be made of two different materials having differing coefficients of elasticity. Returning briefly to FIG. 3, the reader will observe as one example that the first portion of posterior strap 52 (the portion nearest axilla anchor region 56) is relatively thick while the remaining portion is thinner (near hook panel 53). The thick portion can be made of a material having a greater resistance to stretching. This allows the technician applying the device to gain a coarse level of adjustment with the thick portion and a fine level of adjustment using the thin portion.

Returning now to FIG. 9, the reader should bear in mind that anchor panel 30 with its attached pivoting buckles represents only one embodiment of the present invention. The important concept is to provide an anchoring point for the anterior and posterior straps in the area of the axilla of the non-affected shoulder. This anchoring point represents a substantial advantage of the present invention.

A tensile connection must be created between the anterior strap and the anchoring point, and the posterior strap and the anchoring point. This may of course be done in a variety of ways. The use of a buckle or loop at the anchoring point allows the straps to be passed through such a loop and then pulled taut. It is also possible to simply connect the free end of each strap directly to the anchoring point.

Figure 10:
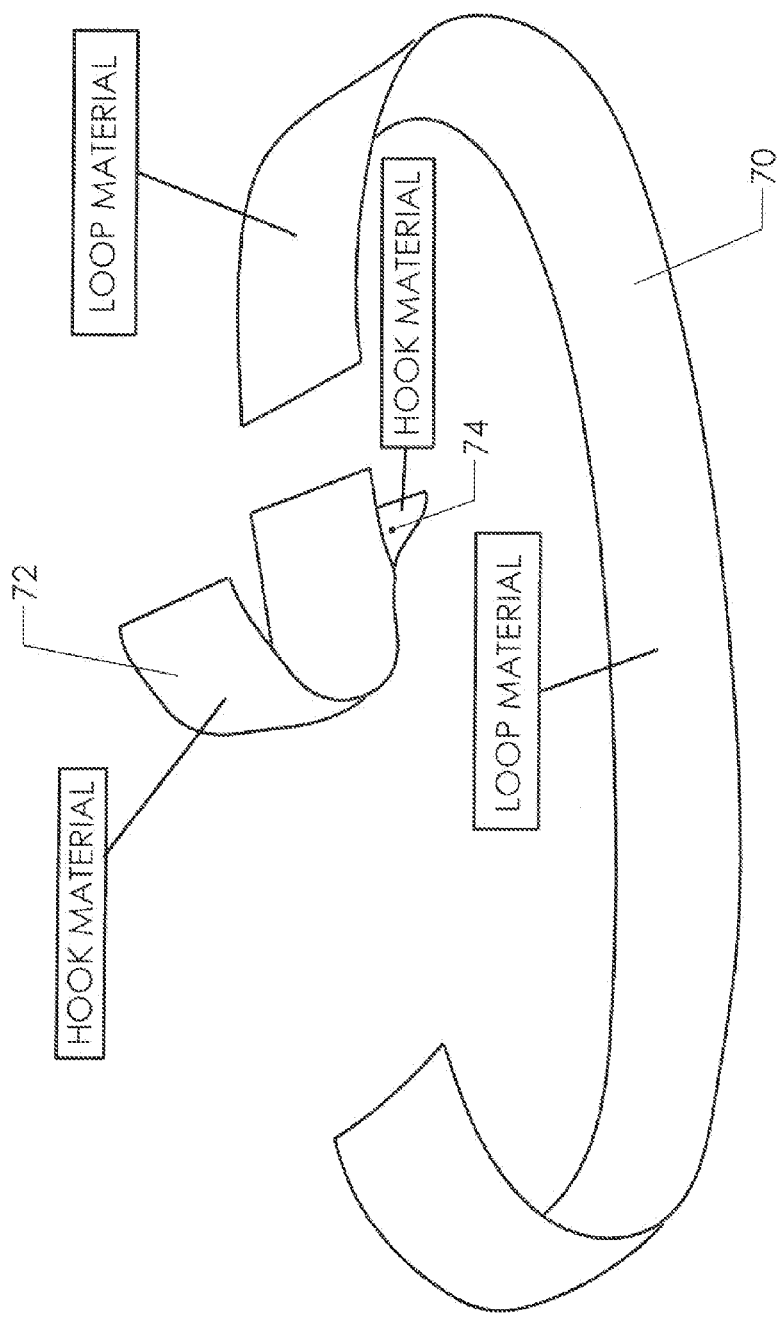
FIG. 10 is a perspective view, showing the components of the invention's top layer.

The next step involves the application of a third layer to the orthotic. FIG. 10 shows this third layer, which is known as A/P strap 70 ("A/P" is short for "anterior/posterior"). A/P strap 70 is a wide elastic band which is preferably covered in loop material on both sides. Butterfly hook panel 72 is designed to attach to the distal end of A/P strap 70, while the proximal end attaches to base harness 10. Butterfly hook panel 72 includes a butterfly 74 which—as those skilled in the art will know—is a pair of inward facing hook panels. The user places butterfly 74 over the distal end of the A/P strap, the presses inward so that the hook panels in butterfly 74 engage the exterior loop material on the A/P strap, thereby securing butterfly hook panel 72 to the A/P strap.

Figure 11:
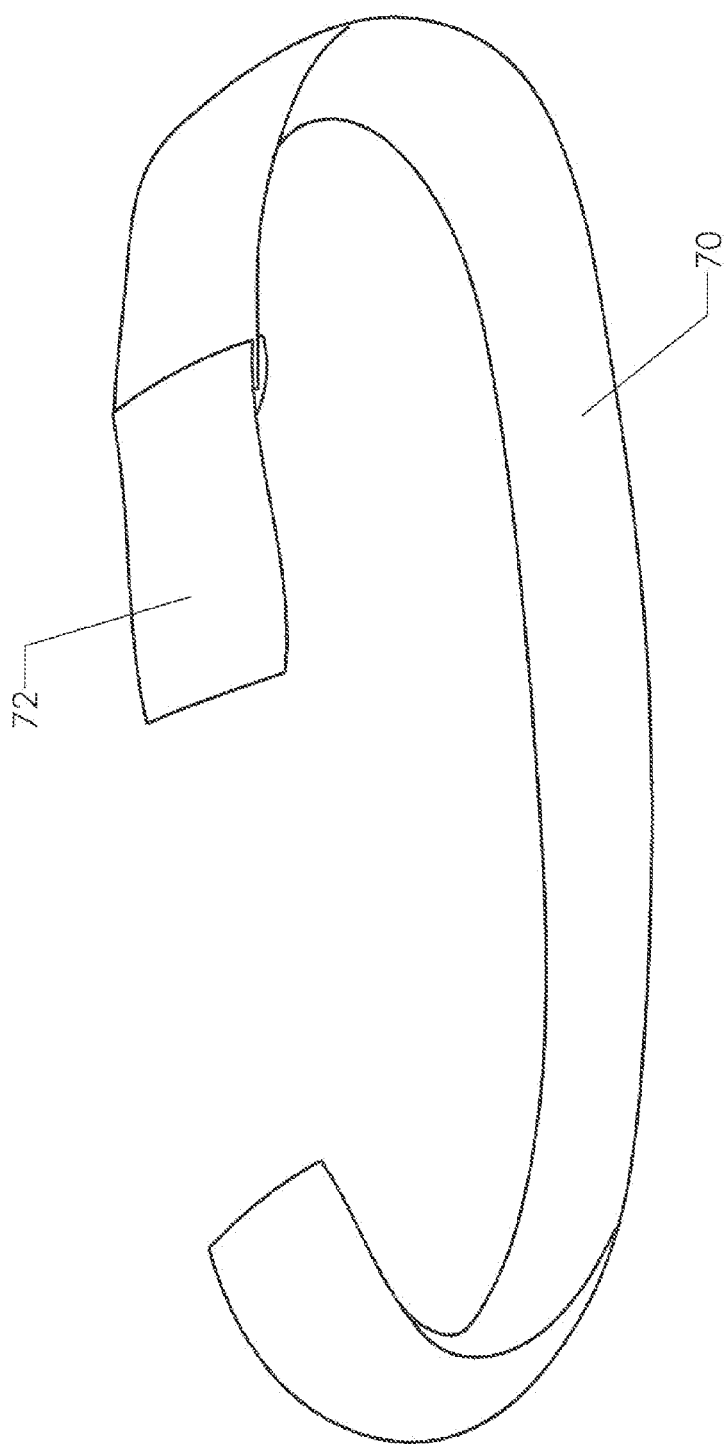
FIG. 11 is a perspective view, showing the components of FIG. 10 in an assembled state.

The use of the separate butterfly hook panel allows a user to trim the A/P strap to a desired length before placing the butterfly hook panel on its end. The hook material on the butterfly hook panel may then be used to secure the distal end of A/P strap 70 in position, as will be explained. FIG. 11 shows A/P strap 70 trimmed to length and with butterfly hook panel 72 installed.

Figure 12:
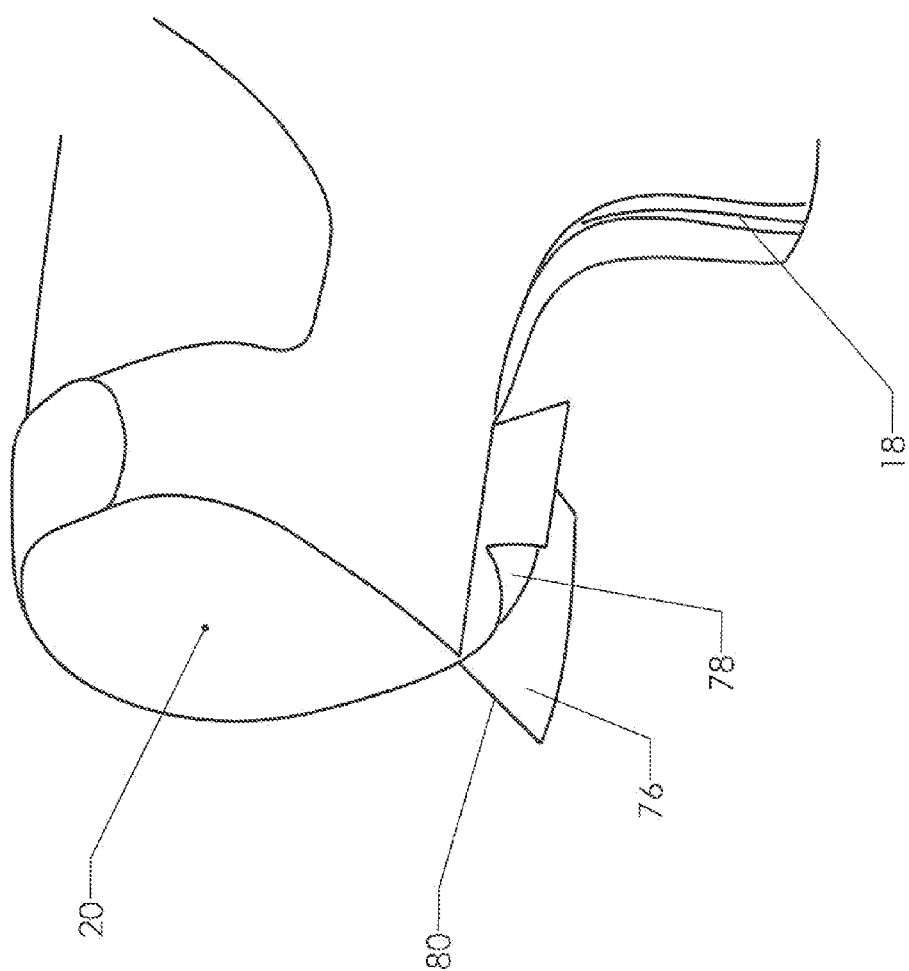
FIG. 12 is a detailed perspective view, showing the shoulder enclosure.

FIG. 12 shows the underside of bicep opening 20 in the shoulder stabilizing orthosis 62. The reader will observe the presence of ventral attachment 80, which is located on the underside of the arm of the affected shoulder. In this example, ventral attachment 80 comprises a pair of inward facing hook panels in a "butterfly" arrangement. These are labeled as hook panel 76 and hook panel 78. The user places the proximal end of A/P strap 70 between these two hook panels and then presses them together. The two hook panels engage the loop material covering the exterior of the A/P strap, thereby attaching the A/P strap to the underside of shoulder enclosure 29. The A/P strap is then attached only at the proximal end, with the balance of the strap hanging loose.

The application of the A/P strap is dependent upon the shoulder condition being treated, and will therefore depend upon the discretion of the healthcare provider affixing the orthosis. Having said that, however, some general principles will apply to certain conditions and the reader may well benefit from an explanation of these general principles. The reader should bear in mind that only a few examples among many, many possibilities are provided.

Figure 13:
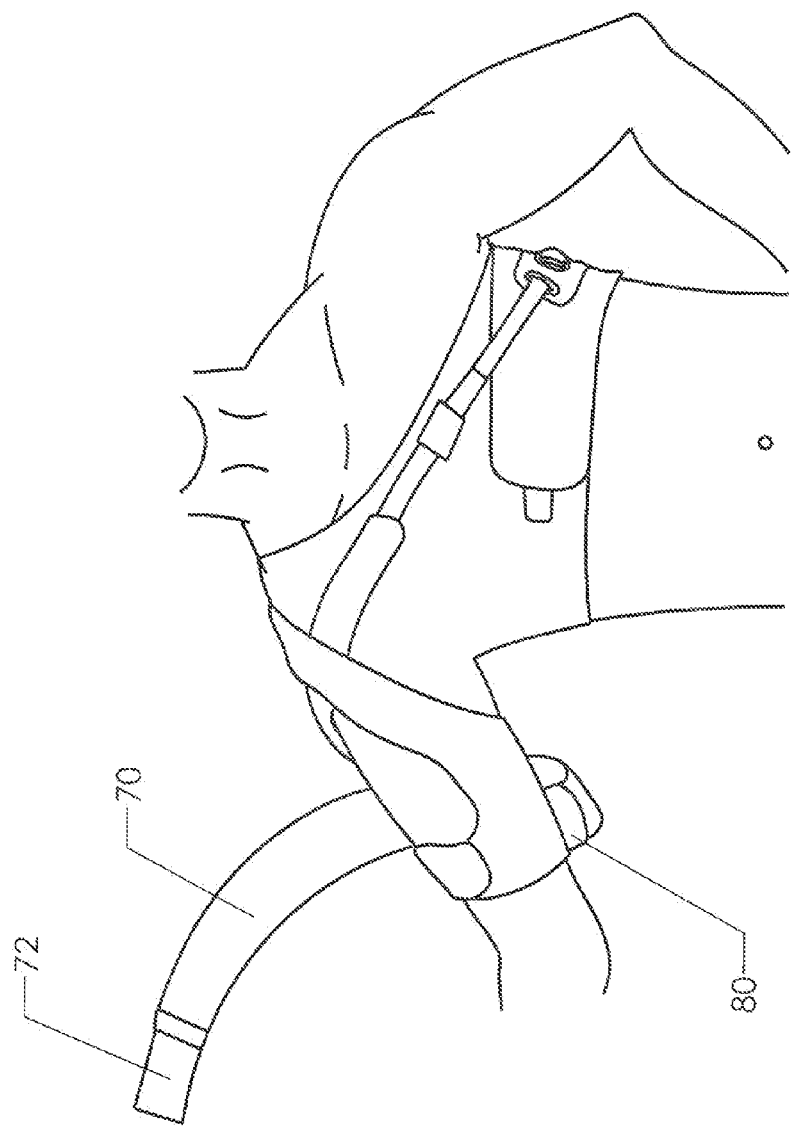
FIG. 13 is an anterior elevation view, showing the application of the A/P strap for anterior instabilities.
Figure 14:
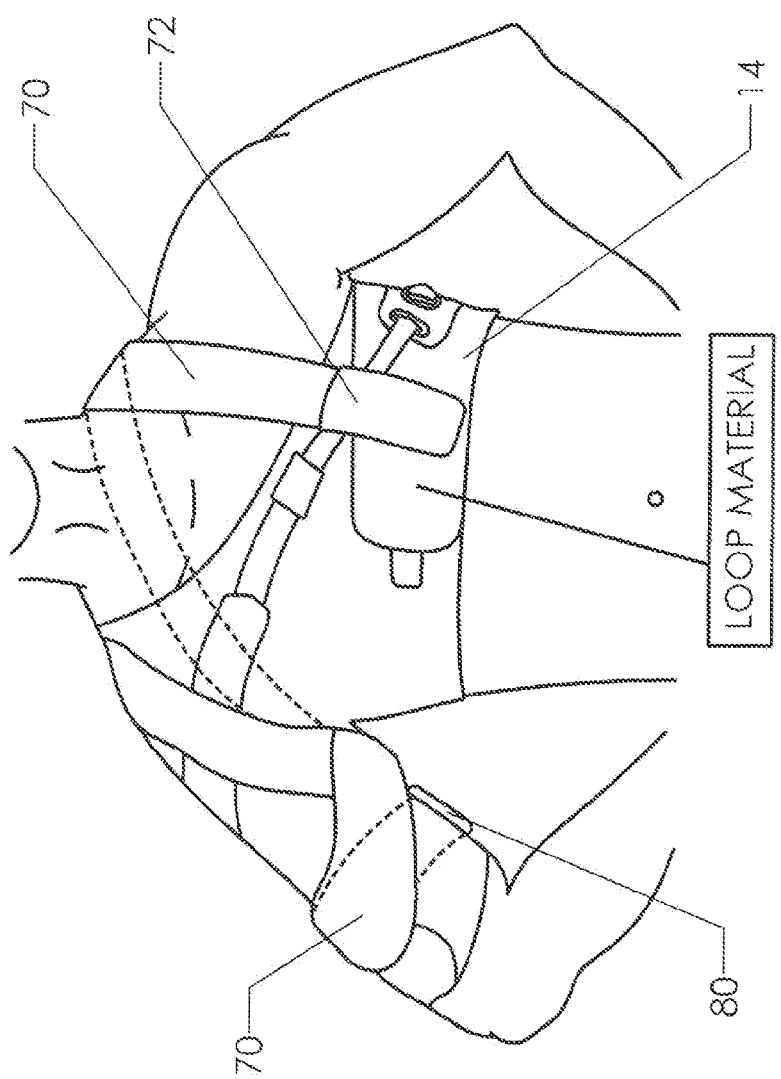
FIG. 14 is an anterior elevation view, showing the application of the A/P strap for anterior instabilities.

One condition to which the orthosis may be applied is an anterior shoulder instability. FIGS. 13 and 14 illustrate this scenario. In FIG. 13, the affected arm is extended outward with the palm of the hand rotated downward. A/P strap 70 is looped around the bicep in a clockwise direction when looking at the arm from the elbow to the shoulder. Prior to securing the A/P strap the hand is brought into the waist and the arm is held in position with the elbow separated from the body as shown in FIG. 14.

The user continues to wrap the A/P strap around the arm in a clockwise direction—adjusting the tension as it is wrapped. The strap is passed under the axilla of the affected shoulder and then across the back (ash shown in dashed lines). The A/P strap is ultimately passed over the trapezius area of the non-affected shoulder and then down over the chest. The strap is secured by pressing butterfly hook panel 72 against the loop material on the exterior of any suitable portion of the orthosis—such as the exterior of posterior panel 14. Anatomical differences will of course dictate the ultimate location of the A/P strap and many variations are possible.

Figure 15:
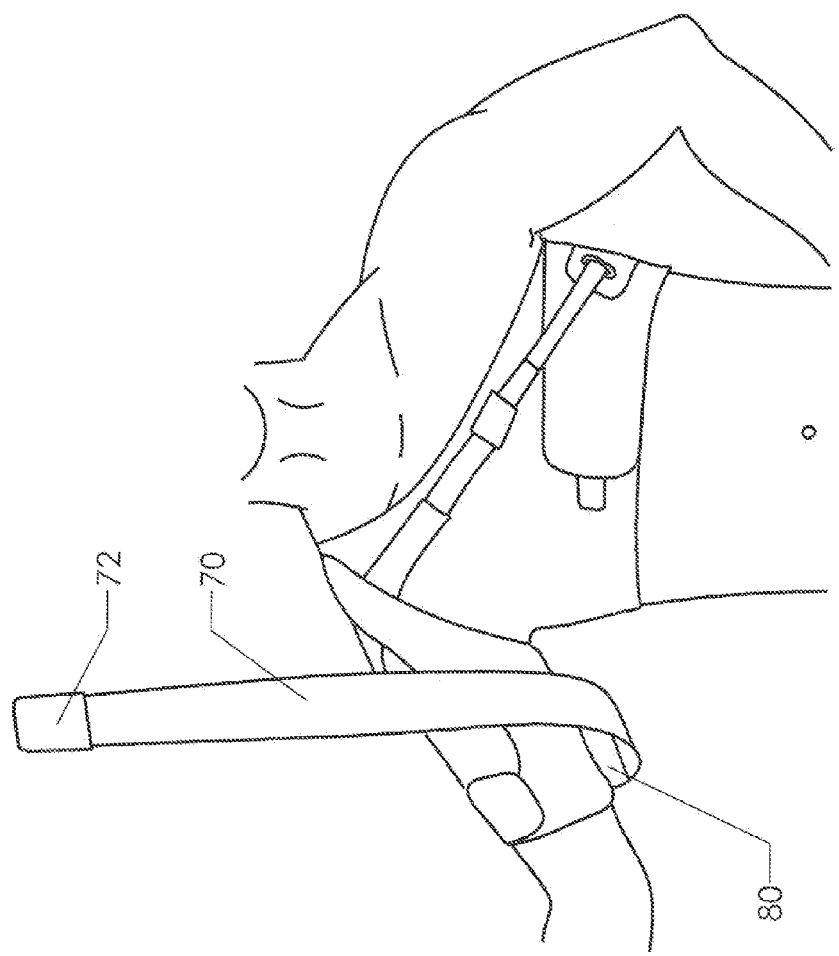
FIG. 15 is an anterior elevation view, showing the application of the A/P strap for posterior instabilities.
Figure 16:
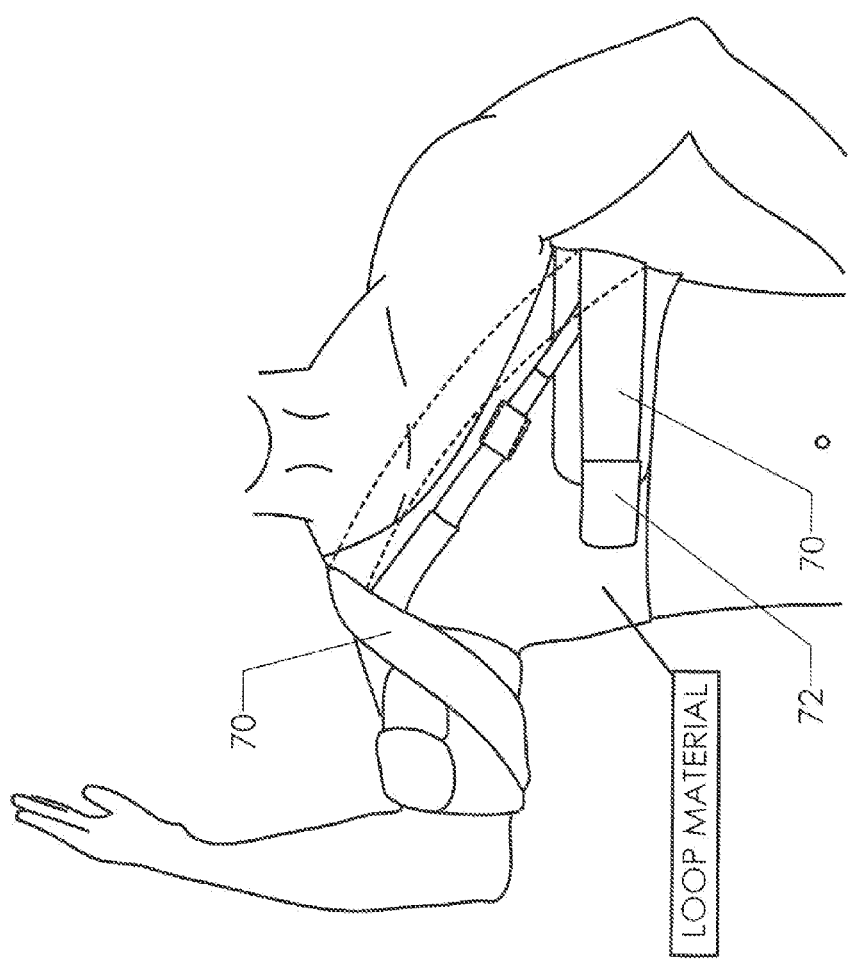
FIG. 16 is an anterior elevation view, showing the application of the A/P strap for posterior instabilities.

FIGS. 15 and 16 illustrate the application of the orthosis for treatment of a posterior instability. The affected arm is held outward with the forearm pointing upward and the thumb of the affected hand facing posteriorly. A/P strap 70 is again attached using ventral attachment 80 as shown. The A/P strap is next looped around the upper arm in a counterclockwise direction when looking from the elbow toward the shoulder.

FIG. 16 shows how A/P strap 70 is wrapped up and over the deltoid region of the affected shoulder. It is then wrapped across the back and under the axilla of the non-affected shoulder. The distal end of the A/P strap is finally attached by pressing butterfly hook panel 72 into the loop material on any appropriate surface of the orthosis.

Figure 17:
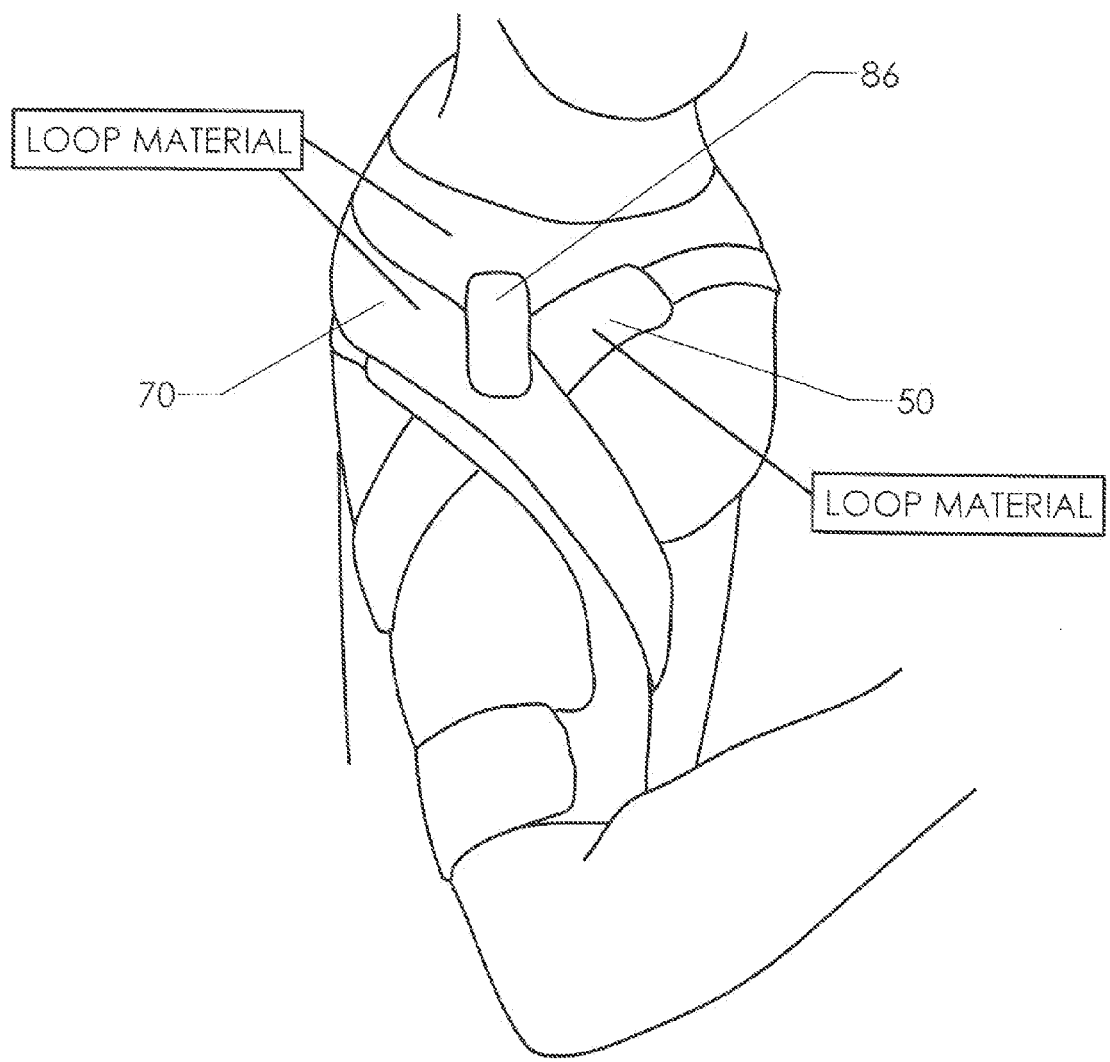
FIG. 17 is a perspective view of the deltoid region of the affected shoulder, showing how the straps are retained in position.

It is preferable that the A/P strap remain in the correct position proximate the deltoid of the affected shoulder. However, the convex shape of the deltoid region means that the A/P strap may tend to slip out of position. It is preferable to add a feature that maintains the desired position. FIG. 17 shows an example of such a feature. FIG. 17 is a lateral perspective view of the deltoid region of a patient's right shoulder. In this example, the A/P strap is wrapped as in FIG. 16. The exterior surfaces of A/P strap 70, anterior strap 50, and posterior strap 52 are preferably all covered in loop material. This fact allows hook panel 86 (which is covered in hooks which face toward the shoulder) to be pressed into the loop material while spanning the edge of the A/P strap. The A/P strap is thereby secured to the base harness and/or the other straps. The straps are thereby secured in the desired position over the deltoid.

Figure 18:
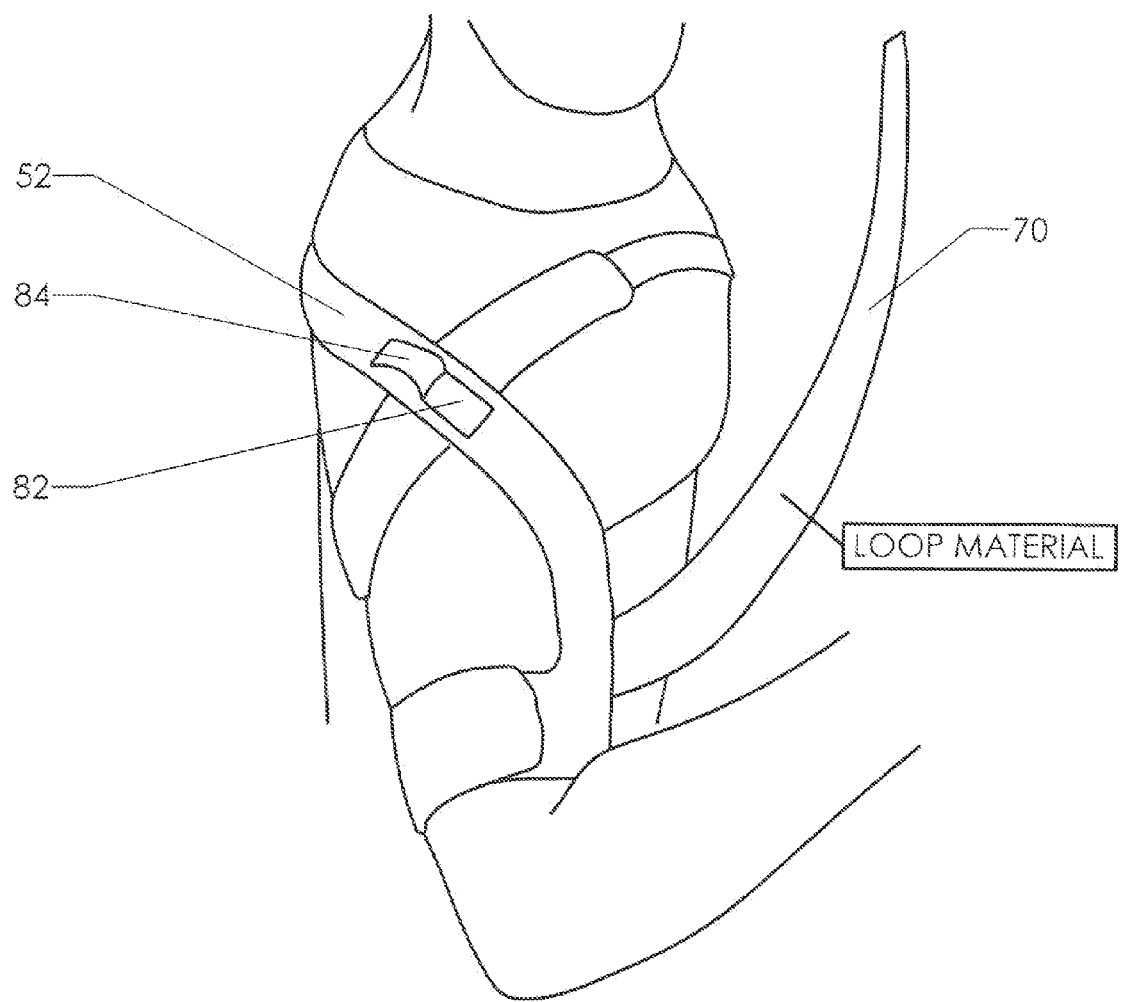
FIG. 18 is a perspective view, showing the use of an integral hook path to secure the straps over the deltoid region.

The use of the separate hook panel 86 may not be optimum, however, since a separate panel can be lost. FIG. 18 shows an alternate embodiment. In this version posterior strap 52 includes an integrated hook patch 82 covered by cover 84. Hook patch 82 is covered in hooks which face away from the shoulder. Cover 84 includes features which hold it out of the way once it has been opened. As A/P strap 70 is wrapped over the deltoid region of the affected shoulder, the loop material on its inward facing surface engages hook patch 82 and thereby retains the A/P strap in the desired position.

The reader will thereby appreciate that the proposed invention has three major layers—the base harness; the anterior and posterior straps; and the A/P strap. Of course, many embodiments would include more than three layers. As an example, if one looks at FIG. 1, the anterior and posterior panels are conveniently made by using two layers—an interior smooth layer and an exterior layer covered in loop material.

The straps are positioned to offer support from multiple angles while still acting in unison. For example, the brace can provide inferior support while at the same time stabilizing anterior or posterior shoulder instabilities. The straps also feature fixed starting points so that a technician may consistently apply them. Finally, some of the straps feature the use of two materials, where the first material is elastic and the second material is not. This allows the technician to more finely adjust the application of the straps.

The orthosis allows the patient nearly a full range of motion. At the same time, the invention prevents the shoulder joint from becoming unstable. An athlete suffering a dislocation injury can continue playing with the orthosis in place without risk of further injury. This fact allows the athlete to defer corrective surgery for a reasonable period of time. The invention is particularly useful for athletes playing American football. The smooth inner layer allows the orthosis to be worn directly against the skin, beneath the undergarments and pads.

Although the preceding description contains significant detail, it should not be viewed as limiting the invention but instead as providing illustrations of the preferred embodiments of the invention. As an example, buckle fasteners could be substituted for the many hook-and-loop engagements used in invention. Many other alterations could be made to the embodiments illustrated without altering the substance of the invention. Thus, the scope of the present invention should be defined by the following claims rather than any specific examples given.

The invention claimed is:

1. A method for stabilizing an affected shoulder joint of a patient, said patient having an affected shoulder with a deltoid region, an axilla, and an upper arm, a non-affected shoulder with an axilla, a chest, and a back, comprising:
   a. providing a base harness having a shoulder enclosure with an axilla anchor region, an anterior panel having a free end, a posterior panel having a free end, and an adjustable break between said free end of said anterior panel and said free end of said posterior panel in a position distal to said shoulder enclosure;
   b. providing a posterior strap, having a proximal end attached to said axilla anchor region and a distal end;
   c. providing an anterior strap, having a proximal end attached to said axilla anchor region and a distal end;
   d. applying said base harness to said patient by sliding said shoulder enclosure over said shoulder joint, wrapping said anterior panel around said chest, and wrapping said posterior panel around said back;
   e. securing said base harness to said patient by attaching said free end of said posterior panel to said free end of said anterior panel;
   f. providing an anchor panel on said base harness, with said anchor panel being positioned so that said anchor panel lies approximately beneath said axilla of said patient's non-affected shoulder;
   g. providing a first buckle and a second buckle on said anchor panel;
   h. passing said posterior strap over said deltoid region of said affected shoulder, across said back, through said first buckle, back across at least a portion of said back, tightening said posterior strap, and securing said distal end of said posterior strap; and
   i. passing said anterior strap over said deltoid region of said affected shoulder, across said chest, through said second buckle, back across at least a portion of said chest, tightening said anterior strap, and securing said distal end of said anterior strap.

2. A method for stabilizing an affected shoulder as recited in claim 1, further comprising:
   a. providing an A/P strap having a proximal end attached to said axilla anchor region of said shoulder enclosure and a free distal end;
   b. wrapping said A/P strap around the posterior portion of said upper arm of said affected shoulder, around the anterior portion of said upper arm, through said axilla of said affected arm, across said back, over said non-affected shoulder, and securing said distal end.

3. A method as recited in claim 2, further comprising securing said anterior strap, said posterior strap, and said A/P strap to said deltoid region of said affected shoulder.

4. A method as recited in claim 2, further comprising interlocking said anterior and posterior straps in said deltoid region of said affected shoulder.

5. A method for stabilizing an affected shoulder as recited in claim 1, further comprising:
   a. providing an A/P strap having a proximal end attached to said axilla anchor region of said shoulder enclosure and a free distal end;
   b. wrapping said A/P strap around the anterior portion of said upper arm of said affected shoulder, over said deltoid region of said affected shoulder, across said back, around said axilla of said non-affected shoulder.

6. A method as recited in claim 5, further comprising securing said anterior strap, said posterior strap, and said A/P strap to said deltoid region of said affected shoulder.

7. A method as recited in claim 5, further comprising interlocking said anterior and posterior straps in said deltoid region of said affected shoulder.

8. A method as recited in claim 1, further comprising securing said anterior and said posterior straps to said deltoid region of said affected shoulder.

9. A method as recited in claim 1, further comprising interlocking said anterior and posterior straps in said deltoid region of said affected shoulder.

10. A method for stabilizing an affected shoulder joint of a patient, said patient having an affected shoulder with a deltoid region, an axilla, and an upper arm, a non-affected shoulder with an axilla, a chest, and a back, comprising:
    a. providing a base harness having a shoulder enclosure with an axilla anchor region, an anterior panel having a free end covered with loop material, and a posterior panel having a free end with an inward facing hook panel;
    b. providing a posterior strap, having a proximal end attached to said base harness proximate to said shoulder enclosure and a distal end;
    c. providing an anterior strap, having a proximal end attached to said base harness proximate to said shoulder enclosure and a distal end;
    d. applying said base harness to said patient by sliding said shoulder enclosure over said shoulder joint, wrapping said anterior panel around said chest, and wrapping said posterior panel around said back;
    e. securing said base harness to said patient by pressing said hook panel on said free end of said anterior panel into said loop material on said posterior panel;
    f. providing an anchor panel on said base harness, with said anchor panel being positioned so that said anchor panel lies approximately beneath said axilla of said patient's non-affected shoulder;
    g. providing a first buckle and a second buckle on said anchor panel;
    h. passing said posterior strap over said deltoid region of said affected shoulder, across said back, through said first buckle, back across at least a portion of said back, tightening said posterior strap, and securing said distal end of said posterior strap; and
    i. passing said anterior strap over said deltoid region of said affected shoulder, across said chest, through said second buckle, back across at least a portion of said chest, tightening said anterior strap, and securing said distal end of said anterior strap.

11. A method for stabilizing an affected shoulder as recited in claim 10, further comprising:
    a. providing an A/P strap having a proximal end attached to said axilla anchor region of said shoulder enclosure and a free distal end;
    b. wrapping said A/P strap around the posterior portion of said upper arm of said affected shoulder, around the anterior portion of said upper arm, through said axilla of said affected arm, across said back, over said non-affected shoulder, and securing said distal end.

12. A method as recited in claim 11, further comprising securing said anterior strap, said posterior strap, and said A/P strap to said deltoid region of said affected shoulder.

13. A method as recited in claim 11, further comprising interlocking said anterior and posterior straps in said deltoid region of said affected shoulder.

14. A method for stabilizing an affected shoulder as recited in claim 10, further comprising:
    a. providing an A/P strap having a proximal end attached to said axilla anchor region of said shoulder enclosure and a free distal end;
    b. wrapping said A/P strap around the anterior portion of said upper arm of said affected shoulder, over said deltoid region of said affected shoulder, across said back, around said axilla of said non-affected shoulder.

15. A method as recited in claim 14, further comprising securing said anterior strap, said posterior strap, and said A/P strap to said deltoid region of said affected shoulder.

16. A method as recited in claim 14, further comprising interlocking said anterior and posterior straps in said deltoid region of said affected shoulder.

17. A method as recited in claim 10, further comprising securing said anterior and said posterior straps to said deltoid region of said affected shoulder.

18. A method as recited in claim 10, further comprising interlocking said anterior and posterior straps in said deltoid region of said affected shoulder.

19. A method for stabilizing an affected shoulder joint of a patient, said patient having an affected shoulder with a deltoid region, an axilla, and an upper arm, a non-affected shoulder with an axilla, a chest, and a back, comprising:
    a. providing a base harness having a shoulder enclosure with an axilla anchor region, an anterior panel having a free end covered with loop material, and a posterior panel having a free end with an inward facing hook panel;
    b. providing a posterior strap, having a proximal end attached to said base harness proximate to said shoulder enclosure and a distal end;
    c. providing an anterior strap, having a proximal end attached to said base harness proximate to said shoulder enclosure and a distal end;
    d. applying said base harness to said patient by sliding said shoulder enclosure over said shoulder joint, wrapping said anterior panel around said chest, and wrapping said posterior panel around said back;
    e. securing said base harness to said patient by pressing said hook panel on said free end of said anterior panel into said loop material on said posterior panel;
    f. providing an anchor point on said base harness, with said anchor point being positioned so that said anchor point lies approximately beneath said axilla of said patient's non-affected shoulder;
    g. passing said posterior strap over said deltoid region of said affected shoulder, across said back, and creating a tensile connection between said posterior strap and said anchor point; and
    h. passing said anterior strap over said deltoid region of said affected shoulder, across said chest, and creating a tensile connection between said anterior strap and said anchor point.

20. A method for stabilizing an affected shoulder as recited in claim 19, further comprising:

a. providing an A/P strap having a proximal end attached to said axilla anchor region of said shoulder enclosure and a free distal end;
b. wrapping said A/P strap around the posterior portion of said upper arm of said affected shoulder, around the anterior portion of said upper arm, through said axilla of said affected arm, across said back, over said non-affected shoulder, and securing said distal end.

21. A method as recited in claim 20, further comprising securing said anterior strap, said posterior strap, and said A/P strap to said deltoid region of said affected shoulder.

22. A method as recited in claim 20, further comprising interlocking said anterior and posterior straps in said deltoid region of said affected shoulder.

23. A method for stabilizing an affected shoulder as recited in claim 19, further comprising:
a. providing an A/P strap having a proximal end attached to said axilla anchor region of said shoulder enclosure and a free distal end;
b. wrapping said A/P strap around the anterior portion of said upper arm of said affected shoulder, over said deltoid region of said affected shoulder, across said back, around said axilla of said non-affected shoulder.

24. A method as recited in claim 23, further comprising securing said anterior strap, said posterior strap, and said A/P strap to said deltoid region of said affected shoulder.

25. A method as recited in claim 23, further comprising interlocking said anterior and posterior straps in said deltoid region of said affected shoulder.

26. A method as recited in claim 19, further comprising securing said anterior and said posterior straps to said deltoid region of said affected shoulder.

27. A method as recited in claim 19, further comprising interlocking said anterior and posterior straps in said deltoid region of said affected shoulder.

\* \* \* \* \*